United States Patent [19]
Choi et al.

[11] Patent Number: 5,914,402
[45] Date of Patent: Jun. 22, 1999

[54] PROCESS FOR PREPARING 1-ARYL-4-OXOPYRROLO [3,2-C] QUINOLINE DERIVATIVES

[75] Inventors: Joong Kwon Choi; Sung Soo Kim; Eul Kyun Yum; Sung Yun Cho; Seung Kyu Kang, all of Taejon-si, Rep. of Korea

[73] Assignee: Korea Research Institute of Chemical Technology, Taejon-si, Rep. of Korea

[21] Appl. No.: 08/983,388

[22] PCT Filed: May 2, 1997

[86] PCT No.: PCT/KR97/00074

§ 371 Date: Jan. 16, 1998

§ 102(e) Date: Jan. 16, 1998

[87] PCT Pub. No.: WO97/44342

PCT Pub. Date: Nov. 27, 1997

[30] Foreign Application Priority Data

May 17, 1996 [KR] Rep. of Korea ........................ 96/16624

[51] Int. Cl.$^6$ ..................... C07D 471/04; C07D 491/048
[52] U.S. Cl. .................................................. 546/81; 546/89
[58] Field of Search ......................................... 546/81, 89

[56] References Cited

U.S. PATENT DOCUMENTS 5,420,135  5/1995  Brown et al. ........................... 514/293

FOREIGN PATENT DOCUMENTS 0307078  3/1989  European Pat. Off. .

OTHER PUBLICATIONS

Leach CA et al. J. Med. Chem. 35, 1845–52, 1992.

*Primary Examiner*—Evelyn Mei Huang
*Attorney, Agent, or Firm*—Dilworth & Barrese

[57] ABSTRACT

The present invention relates to a process for preparing 1-aryl-4-oxopyrrolo[3,2-c]quinoline derivatives through reaction of 4-oxofuro[3,2-c] quinoline compounds with aniline compounds under mild conditions in a single step, wherein 1-aryl-4-oxopyrrolo[3,2-c]quinoline derivatives having various substituents may be prepared in high yield, so that the 1-aryl-4-oxopyrrolo[3,2-c]quinoline derivatives may be utilized as an intermediate for producing a reversible inhibitor of gastric acid secretion.

18 Claims, No Drawings

PROCESS FOR PREPARING 1-ARYL-4-OXOPYRROLO [3,2-C] QUINOLINE DERIVATIVES

This application is the national phase of PCT/KR,97/00074, filed on May 2, 1997, published as WO97/44342 on Nov. 27, 1997.

FIELD OF THE INVENTION

The present invention relates to a process for preparing 1-aryl-4-oxopyrrolo[3,2-c]quinoline derivatives and, more particularly, to a process for preparing 1-aryl-4-oxopyrrolo[3,2-c]quinoline derivatives represented by structure I which is prepared through the reaction of 4-oxofuro[3,2-c]quinolines with anilines represented by structure III. The formulae I, II and III are as follows:

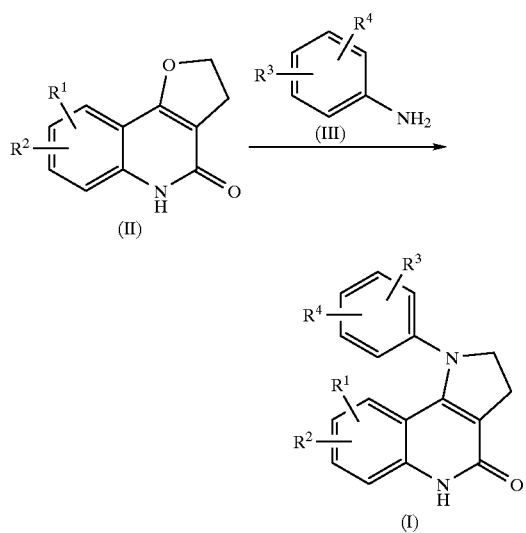

wherein, $R^1$ may be same or different from $R^2$ which are respectively hydrogen, lower alkyl group of $C_1$–$C_4$, lower alkoxy group of $C_1$–$C_4$, lower alkylthio group of $C_1$–$C_4$, lower haloalkoxy group of $C_1$–$C_4$, trifluoromethyl group, hydroxyalkoxy group of $C_1$–$C_4$, halogen, or hydroxy group; and $R^3$ may be same or different from $R_4$ which are respectively hydrogen, lower alkyl group of $C_1$–$C_4$, lower alkoxy group of $C_1$–$C_4$, lower alkylthio group of $C_1$–$C_4$, lower haloalkyl group of $C_1$–$C_4$, trifluoromethyl group, hydroxy group, amino group, or halogen.

The 1-aryl-4-oxopyrrolo[3,2-c]quinoline derivatives which are prepared according to the present invention are used as intermediates for preparing compounds as represented by structure IV for suppressing gastric acid secretion and many studies have been carried out to prepare the intermediate so far [European Patent Application No. 90-313398.1; European Patent Application No. 88-306583.1; J. Med. Chem., 1990, 33, 527; J. Med. Chem., 1992, 35, 1845].

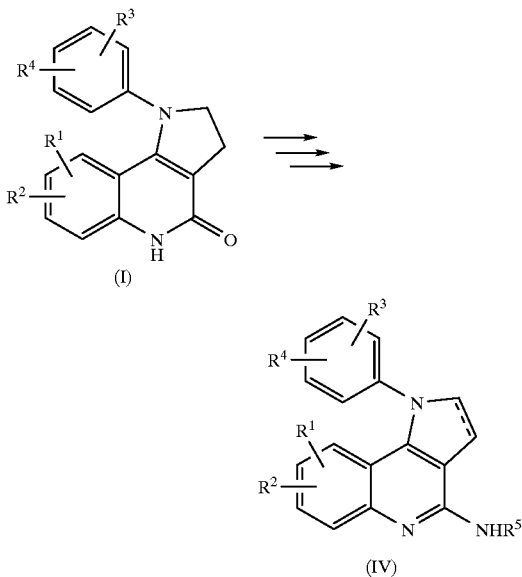

The present invention is to provide a process for preparing compounds as represented by the above structure I which are intermediates in preparation of compounds as represented by the above structure IV which are useful as repressor of the gastric acid secretion.

The present invention is to provide a process for preparing compounds as represented by the above formula IV by using the 1-aryl-4-oxopyrrolo[3,2-c]quinoline derivatives which can be prepared in a single reaction step from 4-oxofuro[3,2-c]quinoline with anilines III.

PRIOR ART

European Patent Application No. 88-306583.1 and an article [J. Med. Chem., 1992, 35, 1845] disclose a process for preparing 1-aryl-4-oxopyrrolo[3,2-c]quinoline derivatives as represented by the above structure I, which may be summarized as follows:

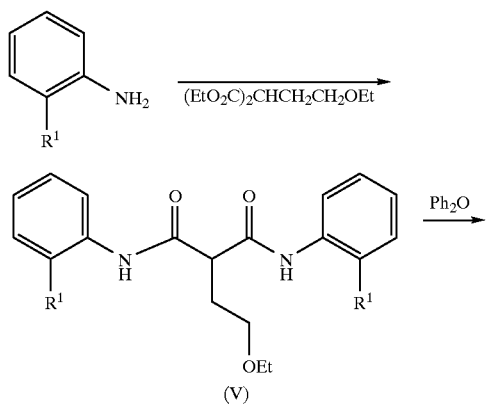

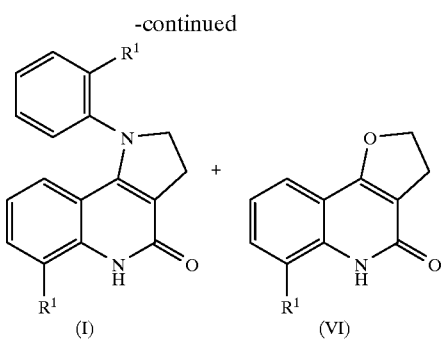

(I)             (VI)

According to the prior art, the 1-aryl-4-oxo pyrrolo[3,2-c]quinoline derivatives I is prepared through reaction of $(EtO_2C)_2CHCH_2CH_2OEt$ with anilines as starting material.

This method has, however, disadvantages that yield is low while producing the compound I and a large amount of the compounds VI is formed as a by-product.

Further, the method has an inherent limitation that substituents are limited to $R^1$ initially present in the starting anilines, and it is impossible to prepare derivatives which has variable substituents.

On the other hand, an article [J. Med. Chem., 1992, 35, 1845] discloses a process for preparing compounds I having substituents $R^1$, $R^2$, $R^3$ and $R^4$, which may be summarized as follows:

and $R^4$ through the reaction of various anilines with the compounds VII.

The method has still disadvantages that a great amount of very toxic $POCl_3$ has to be used as a reaction reagent and yields are relatively low about 50–70% in each reaction steps. Further, the compound I was obtained in mere prepared 20% yield due to the rather lengthy reaction steps from the compound II.

Therefore, the present inventors have developed a novel process to resolve the disadvantages of prior art and to prepare the compounds IV with high biological activity and various substituents through environmentally friendly and simple steps.

As a result, the quinoline compound IV may be prepared in a high yield by using 1-aryl-4-oxopyrrolo[3,2-c]quinoline derivatives which may be prepared conveniently in a high yield in such a manner that 4-oxofuro[3,2-c]quinolines II as starting material are reacted with various anilines as reactant in a single step.

SUMMARY OF THE INVENTION

The present invention has an objective to provide a process for preparing 1-aryl-4-oxopyrrolo[3,2-c]quinoline derivatives I through a single step to react 4-oxofuro[3,2-c]quinolines II as a starting material with aniline III.

The present invention has another objective to provide a process for preparing quinoline compounds IV by using the 1-aryl-4-oxopyrrolo[3,2-c]quinoline derivatives.

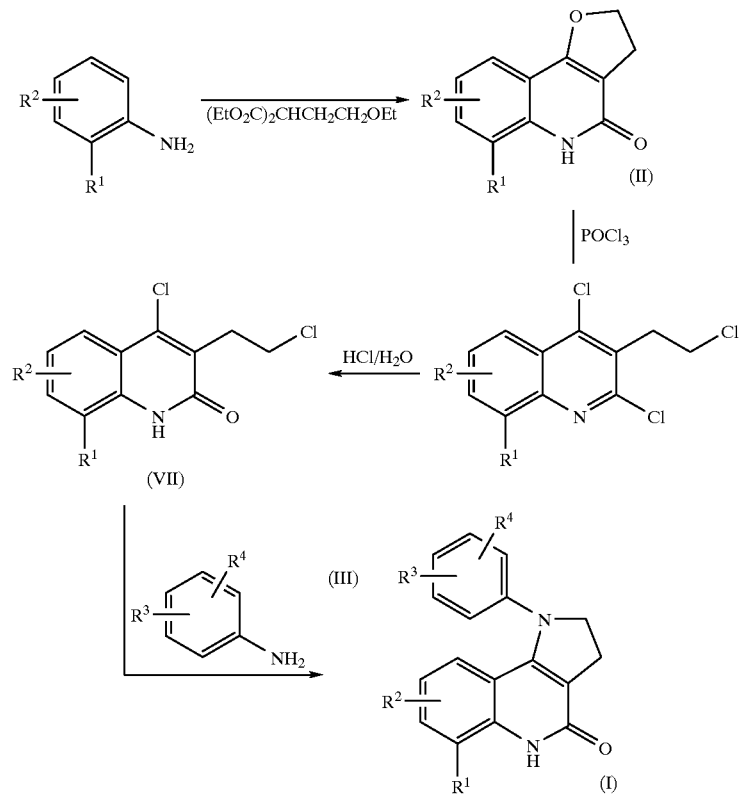

According to the above method, 4-oxofuro[3,2-c] quinolines are chlorinated with $POCl_3$ and subject to hydrolysis to obtain compounds VII, so that 1-aryl-4-oxopyrrolo[3,2-c] quinoline derivatives I having the substituents $R^1$, $R^2$, $R^3$ According to the present invention, the above objective can be achieved by a process for preparing 1-aryl-4-oxopyrrolo[3,2-c]quinoline derivatives by reacting 4-oxofuro[3,2-c]quinolines with anilines under a gentle condition in a single step, wherein 1-aryl-4-oxopyrrolo[3,2-c]quinoline derivatives having various substituents may be obtained in high yield, so that the 1-aryl-4-oxopyrrolo[3,2-c]quinoline derivatives may be utilized as intermediate for producing a reversible inhibitor of gastric acid secretion.

DETAILED DESCRIPTION OF THE INVENTION

The present invention will now be described in detail with reference to the schemes showing embodiments thereof.

The present invention relates to a method of preparing 1-aryl-4-oxopyrrolo[3,2-c]quinoline derivatives represented by structure I which are useful intermediate for compounds represented by structure IV with high biological activity, wherein the 1-aryl-4-oxopyrrolo[3,2-c]quinoline derivatives are prepared by the reaction of aniline compounds represented by structure III with 4-oxofuro[3,2-c]quinolines represented by structure II as starting material.

According to the present invention, the 1-aryl-4-oxopyrrolo[3,2-c]quinoline derivatives with various substituents $R^1$, $R^2$, $R^3$ and $R^4$ may be prepared in higher than 70% of yield.

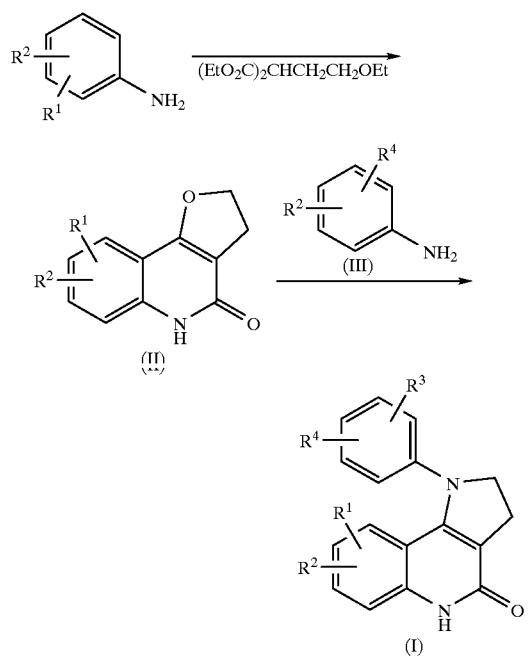

In the formulae I, II and III, substituents $R^1$, $R^2$, $R^3$ and $R^4$ are defined as above.

The preparation of substituted quinoline compounds, 4-oxofuro[3,2-c]quinoline derivatives II used as starting material are well described in the prior art [1, J. Chem. Sec., 1955, 4284; 2. J. Med. Chem., 1992, 35, 1845].

According to the present invention, solvent is selected from those such as dimethylformamide, dimethyl sulfoxide, diphenyl ether, xylene and the like, or alcoholic solvents such as butyl alcohol, phenol, ethylene glycol monomethyl ether and the like. Preferably, the solvent is selected from alcoholic solvents of which boiling point is 150°–280° C., such as phenol, ethylene glycol, diethylene glycol or polyethylene glycol.

The process for preparing 1-aryl-4-oxopyrrolo[3,2-c]quinoline derivatives according to the present invention is preferably performed under inert atmosphere, such as argon or nitrogen.

As a reaction catalyst, p-toluenesulfonic acid and p-toluenesulfonic acid pyridine salt (PPTS) may be used.

Reaction temperature is preferably maintained at 70°–300° C., and more preferably, 150°–280° C., and reaction time is preferably 7–20 hours.

One to three equivalents of the anilines, as represented by structure III, is effective for preparation of 4-oxopyrrolo[3,2-c]quinolines as represented by structure II.

Typical examples of the 1-aryl-4-oxopyrrolo[3,2-c]quinoline derivatives as represented by structure I according to the present invention are shown in table 1, as follows:

TABLE 1

| No. | $R^1/R^2$ | $R^3/R^4$ |
|---|---|---|
| 1 | H | 2-$CH_3$ |
| 2 | H | 2-$OCH_3$ |
| 3 | H | 2-$CH_3$/4-$OCH_3$ |
| 4 | 6-$CH_3$ | H |
| 5 | 6-$CH_3$ | 2-$CH_3$ |
| 6 | 6-$CH_3$ | 2-$OCH_3$ |
| 7 | 6-$CH_3$ | 2-$CH_3$/4-$OCH_3$ |
| 8 | 6-$CH_3$ | 2-$CH_3$/4-OH |
| 9 | 6-$CH_3$ | 2-$CH_3$/4-F |
| 10 | 6-$CH_3$ | 2-$CH_3$/4-$CH_3$ |
| 11 | 6-$CH_3$ | 2-$CH_2CH_3$ |
| 12 | 6-$OCH_3$ | H |
| 13 | 6-$OCH_3$ | 2-$CH_3$ |
| 14 | 6-$OCH_3$ | 2-$OCH_3$ |
| 15 | 6-$OCH_3$ | 2-$CH_3$/4-$OCH_3$ |
| 16 | 6-$OCH_3$ | 2-$CH_3$/4-OH |
| 17 | 6-$OCH_3$ | 2-$CH_3$/4-F |
| 18 | 6-$OCH_3$ | 2-$CH_3$/6-$CH_3$ |
| 19 | 6-$OCH_3$ | 3-$CH_3$ |
| 20 | 6-F | 2-$CH_3$ |
| 21 | 6-F | 2-$OCH_3$ |
| 22 | 6-$CF_3$ | 2-$CH_3$ |
| 23 | 6-$OCF_3$ | H |
| 24 | 6-$OCF_3$ | 2-$CH_3$ |
| 25 | 6-$OCF_3$ | 2-$OCH_3$ |
| 26 | 6-$OCF_3$ | 2-$CH_3$/4-$OCH_3$ |
| 27 | 6-$OCF_3$ | 2-$CH_3$/4-OH |
| 28 | 6-$OCF_3$ | 2-$CH_3$/4-F |
| 29 | 6-$OCF_3$ | 2-$CH_3$/6-$CH3$ |
| 30 | 6-$OCH_2F_3$ | 2-$CH_3$ |
| 31 | 6-$OCH_2CF_3$ | 2-$CH_3$/4-OH |
| 32 | 6-$SCH_3$ | 2-$CH_3$ |
| 33 | 6-$CH_3$/8-$OCH_3$ | 2-$CH_3$ |
| 34 | 6-$CH_3$/8-F | 2-$OCH_3$ |
| 35 | 6-$OCH_3$/7-F | 2-$CH_3$ |
| 36 | 6-OH | 2-$CH_3$ |
| 37 | 6-$OCF_3$/8-$OCH3$ | 2-$CH_3$ |
| 38 | 6-$OCH_2CH_2OH$ | 2-$CH_3$ |
| 39 | 6-$CH_2OH$ | 2-$CH_3$ |
| 40 | 6-CH(OH)$CH_3$ | 2-$CH_3$ |

The 1-aryl-4-oxopyrrolo[3,2-c]quinoline derivatives I which is prepared as above can be used to prepare the compound IV as a reversible inhibitor of the gastric acid secretion through the publicly known method (J. Med. Chem., 1992, 35, 1845)

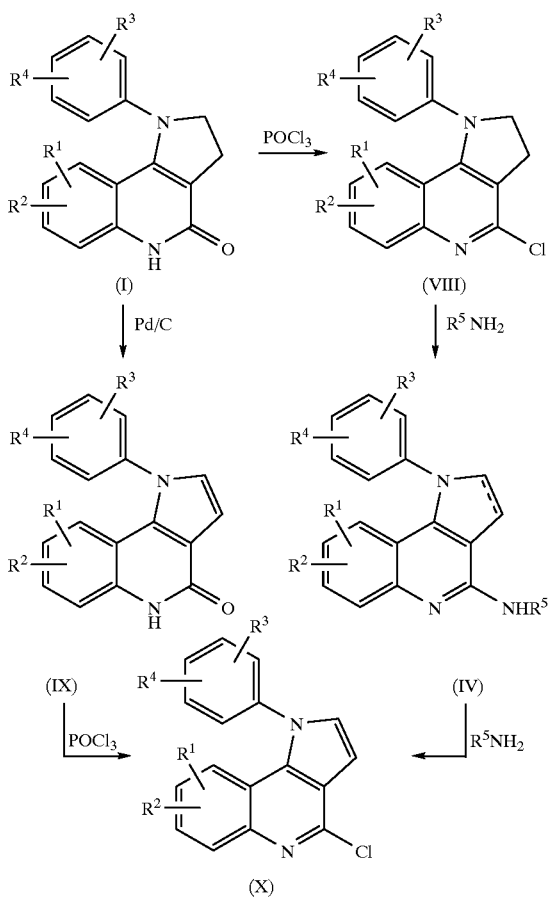

While the invention has been described by reference to specific examples chosen for purposes of illustration, it should be apparent that the present invention be not limited by the specific disclosure herein and numerous modifications could be made thereto by those skilled in the art without departing from the basic concept and scope of the invention.

EXAMPLE 1

Preparation of 1-(2-methylphenyl)-4-oxo-6-methyl-2,3,4,5-tetrahydropyrrolo[3,2-c]quinoline 4-Oxo-6-methyl-2,3-dihydrofuro[3,2-c]quinoline (201 mg, 1.0 mmol) was dissolved in 10 ml of diethylene glycol in a pressure tube and 2-methylaniline (267 μl, 2.5 mmol) was added under nitrogen. The reaction mixture was heated at 250° C. for 15 hours. The reaction mixture was diluted with 20 ml of saline and the aqueous layer was extracted with methylene chloride (15 ml×3). After washing with water (15 ml×3), the organic layer was dried with anhydrous magnesium sulfate and filtered, and concentrated under reduced pressure. The residue was purified with ethyl acetate as eluent by silica gel chromatography to obtain 237 mg of a desired compound as solid in 82 % of yield.

mp: 171°–173° C.

$^1$H NMR(CDCl$_3$, 200 MHz): δ 2.31(s, 3H), 2.44(s, 3H), 3.05–3.38(m, 2H), 3.76(q, 1H), 4.05–4.23(m, 1H), 6.55–6.75(m, 2H), 7.05–7.39(m, 5H), 8.74(brs, 1H)

m/e: 290(M$^+$)

EXAMPLE 2

Preparation of 1-(2-methoxyphenyl)-4-oxo-6-methyl-2,3,4,5-tetrahydropyrrolo[3,2-c]quinoline 4-Oxo-6-methyl-2,3-dihydrofuro[3,2-c]quinoline (201 mg, 1.0 mmol) was dissolved in 10 ml of diethylene glycol and 2-methoxyaniline (282 μl, 2.5 mmol) was added under nitrogen. The reaction mixture was heated at 250° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, and concentrated under reduced pressure. The residue was purified with ethyl acetate as eluent by silica gel chromatography to obtain 242 mg of desired compound as solid in 79% of yield.

mp: 193°–195° C.

$^1$H NMR(CDCl$_3$, 200 MHz): δ 2.39(s, 3H), 3.15–3.29 (m, 2H), 3.74(s, 3H), 3.68–3.85(m, 1H), 4.05–4.27(m, 1H), 6.05–7.40(m, 7H), 8.41(brs, 1H)

m/e: 360(M$^+$)

EXAMPLE 3

Preparation of 1- (2-methyl-4-methoxyphenyl)-4-oxo-6-methyl-2,3,4, 5-tetrahydropyrrolo [3,2-c] quinoline 4-Oxo-6-methyl-2,3-dihydropuro[3,2-c]quinoline (201 mg, 1.0 mmol) was dissolved in 10 ml of diethylene glycol in a pressure tube and 2-methyl-4-methoxyaniline (322 μl, 2.5 mmol) was added under nitrogen. The reaction mixture was heated at 250° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, and concentrated under reduced pressure. The residue was purified with ethyl acetate as eluent by silica gel chromatography to obtain 272 mg of desired compound as solid in 85% of yield.

mp: 210°–213° C.

$^1$H NMR(CDCl$_3$, 200 MHz): δ 2.38(s, 3H), 2.41(s, 3H), 3.07–3.37(m, 2H), 3.68–3.92(m, 1H), 3.83(s, 3H), 4.01–4.18(m, 1H), 6.57–6.89(m, 4H), 7.03–7.29(s, 32H), 8.41(brs, 1H)

m/e: 320(M$^+$)

EXAMPLE 4

Preparation of 1-(2-methyl-4-hydroxyphenyl)-4-oxo-6-methyl-2,3,4,5-tetrahydropyrrolo[3,2-c] quinoline 4-Oxo-6-methyl-2,3-dihydrofuro[3,2-c]quinoline (201 mg, 1.0 mmol) was dissolved in 10 ml of diethylene glycol in a pressure tube and 4-amino-m-cresol (308 mg, 2.5 mmol) was added under nitrogen. The reaction mixture was heated at 250° C. for 15 hours. The reaction mixture was diluted in 20 ml of salt water and the aqueous layer was extracted by methylene chloride (15 ml×3). After washing with water (15 ml×3), the organic layer was dried by anhydrous magnesium sulfate and filtered, and concentrated under reduced pressure. The residue was purified with ethyl acetate as eluent by silica gel chromatography to obtain 210 mg of desired compound as solid in 81% of yield.

mp: 244°–246° C.

¹H NMR(CDCl₃, 200 MHz): δ 2.18(s, 3H), 2.39(s, 3H), 3.05–3.39(m, 2H), 3.74–3.94(m, 1H), 3.98–4.17(m, 1H), 6.63–7.27(m, 6H), 8.55(brs, 1H), 9.49(brs, 1H)

m/e: 306(M⁺)

EXAMPLE 5

Preparation of 1-(phenyl)-4-oxo-6-methoxy-2,3,4,5-tetrahydropyrrolo[3,2-c]quinoline 4-Oxo-6-methoxy-2,3-dihydrofuro[3,2-c]quinoline (217 mg, 1.0 mmol) was dissolved in 7 ml of phenol and aniline (228 μl, 2.5 mmol) was added under nitrogen. The reaction mixture was heated at 190° C. for 15 hours. The reaction mixture was diluted with 20 ml of salt water and the aqueous layer was extracted with methylene chloride (15 ml×3). After washing with water (15 ml×3), the organic layer was dried by anhydrous magnesium surface and filtered, and concentrated under reduced pressure. The residue was purified with ethyl acetate as eluent by silica gel chromatography to obtain 240 mg of desired compound as solid in 83% of yield.

mp: 75°–77° C.

¹H NMR(CDCl₃, 200 MHz): δ 3.12(t, J=9.2 Hz, 2H) 3.89 (s, 3H), 4.03(t, J=9.5 Hz, 2H), 6.50(d, J=7.8 Hz, 1H), 6.71–7.33(m, 7H), 8.91(brs, 1H)

m/e: 292(M⁺)

EXAMPLE 6

Preparation of 1-(2-methylphenyl)-4-oxo-6-methoxy-2,3,4,5-tetrahydropyrrolo[3,2-c]quinoline 4-Oxo-6-methoxy-2,3-dihydrofuro[3,2-c]quinoline (217 mg, 1.0 mmol) was dissolved in 10 ml of diethylene glycol in a pressure tube and 2-methylaniline (267 μl, 2.5 mmol) was added under nitrogen. The reaction mixture was heated at 250° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, amd concentrated under reduced pressure. The residue was purified with ethyl acetate as eluent by silica gel chromatography to obtain 235 mg of desired compound as solid in 77% of yield.

mp: 166°–168° C.

¹H NMR(CDCl₃, 200 MHz): δ 2.34(s, 3H), 3.11–3.41 (m, 2H), 3.72–3.91(m, 1H), 3.97(s, 3H), 4.06–4.28(m, 1H), 6.28(d, J=7.9 Hz, 1H), 6.73(d, J=8.2 Hz, 1H), 6.82(d, J=7.9 Hz, 1H), 7.05–7.42(m, 4H), 8.91(brs, 1H)

m/e: 306(M⁺)

EXAMPLE 7

Preparation of 1-(2-methoxyphenyl)-4-oxo-6-methoxy-2,3,4,5-tetrahydropyrrolo[3,2-c]quinoline 4-Oxo-6-methoxy-2,3-dihydrofuro[3,2-c]quinoline (217 mg, 1.0 mmol) was dissolved in 10 ml of diethylene glycol in a pressure tube and of 2-methylaniline (282 μl, 2.5 mmol) was added under nitrogen. The reaction mixture was heated at 250° C. for 15 hours. The reaction mixture was diluted with 20 ml of salt water and the aqueous layer was extracted with methylene chloride (15 ml×3). After layer with water (15 ml×3), the organic layer was dried with anhydrous magnesium sulfate and filtrated to be concentrated under reduced pressure. The residue was purified with ethyl acetate as a development solution according to silica gel chromatography to obtain 260 mg of desired compound as solid in 81% of yield.

mp: 185°–188° C.

¹H NMR(CDCl₃, 200 MHz): δ 3.18(t, J=9.2 Hz, 2H), 3.70–4.21(m, 2H), 3.73(s, 3H), 6.44(d, J=8.2 Hz, 1H), 6.67–7.34(m, 6H), 8.87(brs, 1H)

m/e: 322(M⁺)

EXAMPLE 8

Preparation of 1-(2-methyl-4-methoxyphenyl)-4-oxo-6-methoxy-2,3,4,5-tetrahydropyrrolo[3,2-c]quinoline 4-Oxo-6-methoxy-2,3-dihydrofuro[3,2-c]quinoline (217 mg, 1.0 mmol) was dissolved in 10 ml of ethylene glycol and 4-methoxy-2-methylaniline (322 μl, 2.5 mmol) was added under nitrogen. The reaction mixture was heated at 210° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, and concentrated under reduced pressure. The residue was purified with ethyl acetate as eluent by silica gel chromatography to obtain 270 mg of desired compound as solid in 81% of yield.

mp: 188°–191° C.

¹H NMR(CDCl₃, 200 MHz): δ 2.23(s, 3H), 3.05–3.35 (m, 2H), 3.80(s, 3H), 3.88(s, 3H), 3.80–4.11(m, 2H), 6.27(dd, J=8.1 Hz, J2=1.1 Hz, 1H), 6.65–6.85(m, 4H), 7.04(d, J=8.6 Hz, 1H), 8.83 (brs, 1H)

m/e: 336(M⁺)

EXAMPLE 9

Preparation of 1-(2-methyl-4-fluorphenyl)-4-oxo-6-methoxy-2,3,4,5-tetrahydropyrrolo[3,2-c]quinoline 4-Oxo-6-methoxy-2,3-dihydrofuro[3,2-c]quinoline (217 mg, 1.0 mmol) was dissolved in 10 ml of diethylene glycol in a pressure tube and (278 μl, 2.5 mmol) of 4-fluor-2-methylaniline (278 μl, 2.5 mmol) was added under nitrogen. The reaction mixture was heated at 250° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, and concentrated under reduced pressure. The residue was purified with ethyl acetate as eluent according to silica gel chromatography to obtain 256 mg of desired compound as solid in 79% of yield.

mp: 195°–198° C.

¹H NMR(CDCl₃, 200 MHz): δ 2.28 (s, 3H), 3.01–3.35 (m, 2H), 3.51–3.82(m, 1H), 3.89 (s, 3H), 3.88–4.15(m, 1H), 6.21(d, J=8.1 Hz, 1H), 6.65–7.14 (m, 5H), 8.89(brs, 1H)

m/e: 324(M⁺)

EXAMPLE 10

Preparation of 1-(3-methylphenyl)-4-oxo-6-methoxy-2,3,4,5-tetrahydropyrrolo[3,2-c]quinoline 4-Oxo-6-methoxy-2,3-dihydrofuro[3,2-c]quinoline (217 mg, 1.0 mmol) was dissolved in 7 ml of phenol in a pressure tube and 3-methylaniline (268 μl, 2.5 mmol) was added under nitrogen. The reaction mixture was heated at 190° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, and concentrated under reduced pressure. The residue was purified with ethyl acetate as eluent by silica gel chromatography to obtain 230 mg of desired compound as solid in 76% of yield.

mp: 155°–157° C.

$^1$H NMR(CDCl$_3$, 200 MHz ): δ2.32(s, 3H), 3.16(t, J=9.2 Hz, 2H), 3.92(s, 3H), 4.06(t, J=9.5 Hz, 2H), 6.56–7.18(m, 6H), 7.24(t, J=6.4 Hz, 1H), 8.91(brs, 1H)

m/e: 306(M$^+$)

EXAMPLE 11

Preparation of 1-(2-methylphenyl)-4-oxo-6-tri fluormethoxy-2,3,4,5-tetrahydropyrrolo[3,2-c] quinoline 4-Oxo-6-trifluormethoxy-2,3-dihydrofuro[3,2-c] quinoline (272 mg, 1.0 mmol) was dissolved in 10 ml of diethylene glycol and 2-methylaniline (267 μl 1.0 mmol) was added under nitrogen. The reaction mixture was heated at 250° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, and concentrated under reduced pressure. The residue was purified with ethyl acetate as eluent by silica gel chromatography to obtain 298 mg of desired compound as solid in 83% of yield.

mp: 153°–156° C.

$^1$H NMR(CDCl$_3$, 200 MHz): δ2.31(s, 3H), 3.10–3.37 (m, 2H), 3.79(q, J=10.2 Hz, 1H), 4.07–4.21(m, 1H), 6.58 (d, J=8.1 Hz, 1H), 6.73(t, J=8.3 Hz, 1H), 7.09–7.36(m, 5H), 8.71(brs, 1H)

m/e: 361(M$^+$)

EXAMPLE 12

Preparation of 1-(2-methoxyphenyl)-4-oxo-6-tri fluormethoxy-2,3,4,5-tetrahydropyrrolo[3,2-c] quinoline 4-Oxo-6-trifluormethoxy-2,3-dihydrofuro[3,2-c] quinoline (272 mg, 1.0 mmol) was dissolved in 10 ml of ethylene glycol in a pressure tube and 2-methoxyaniline (282 μl, 1.0 mmol) was added under nitrogen. The reaction mixture was heated at 210° C. for 15 hours. The reaction mixture was diluted with 20 ml of salt water and the aqueous layer was extracted with methylene chloride (15 ml×3). After washing with water (15 ml×3), the organic layer was dried by anhydrous magnesium sulfate and filtered, and concentrated under reduced pressure. The residue was purified with ethyl acetate as eluent by silica gel chromatography to obtain 286 mg of desired compound as solid in 76% of yield.

mp: 171°–173° C.

$^1$H NMR(CDCl$_3$, 200 MHz): δ3.18–3.31(m, 2H) 3.76 (s, 3H), 3.75–3.95(m, 1H), 4.05–4.27(m, 1H), 6.75–7.48 (m, 7H), 8.83(brs, 1H)

m/e: 377(M$^+$)

EXAMPLE 13

1) Preparation of 1-(4-methoxy-2-methylphenyl)-4-chloro-6-methyl-2,3-dihydropyrrolo[3,2-c]quinoline 1-(4-methoxy-2-methylphenyl)-4-oxo-6-methyl-2,3,4,5-tetrahydropyrrolo[3,2-c]quinoline (1.0 g, 3.1 mmol) was dissolved in 10 ml of phosphoryl chloride (POCl$_3$) and heated for 2 hours. The reaction mixture was stirred at room temperature for 30 minutes after cooling and addition of ice water. The reaction mixture was extracted with methylene chloride (20 ml×3). After washing with water (15 ml×3), the organic layer was dried by anhydrous magnesium sulfate and filtered, and concentrated under reduced pressure. The residue was purified by silica gel chromatography to obtain 786 mg of desired compound as an oil in 75% of yield.

$^1$H NMR(CDCl$_3$, 200 MHz): δ 2.24(s, 3H), 2.65(s, 3H), 3.05–3.35(m, 2H), 3.85(s, 3H), 3.80–4.11(m, 2H), 6.27(dd, J$_1$=8.1 Hz, J$_2$=1.1 Hz, 1H), 6.65–6.89(m, 4H), 7.05(d, J=8.4 Hz, 1H)

m/e: 338(M$^+$)

2) Preparation of 1-(4-methoxy-2-methylamino)-6-methyl-2,3-dihydropyrrolo[3,2-c]quinoline (IV)

1-(4-methoxy-2-methyl phenyl)-4-chloro-6-methyl-2,3-dihydropyrrolo[3,2-c]quinoline (496 mg, 1.2 mmol) was dissolved in 10 ml of ethyl alcohol and 5 ml of 40% aqueous methylamine was added. The reaction mixture was heated at 170° C. for 20 hours in a pressure tube and solvent was distilled under reduced pressure. The reaction mixture was diluted with 20 ml of methylene chloride. After washing with water (15 ml×3), the organic layer was dried by anhydrous magnesium sulfate and filtered, and concentrated under reduced pressure. The residue was purified by silica gel chromatography to obtain 324 mg of desired compound in 81% of yield.

$^1$H NMR(CDCl$_3$, 200 MHz): δ2.27(s, 3H), 2.64(s, 3H), 2.91–3.20(m, 2H), 3.11(d, 3H), 3.65–3.82(m, 1H), 3.81(s, 3H), 4.03–4.21(m, 2H), 6.68–6.81(m, 3H), 6.83–6.90(m, 2H), 7.20–7.31(m, 1H)

m/e: 333(M$^+$)

EXAMPLE 14

1) Preparation of 1-(2-methylphenyl)-4-oxo-6-methyl-4,5-dihydropyrrolo[3,2-c]quinoline (IX)

1-(2-methylphenyl)-4-oxo-6-methyl-2,3,4,5-tetra hydropyrrolo[3,2-c]quinoline (290 mg, 1.0 mmol) was dissolved in 20 ml of diphenyl ether and 40 mg of 5% palladium/carbon was added. The reaction mixture was heated for 4 hours. The reaction mixture was cooled to the room temperature and directly purified by silica gel chromatography to obtain 245 mg of desired compound as solid in 85% of yield.

mp:224°–227° C.

$^1$H NMR(CDCl$_3$, 200 MHz): δ 1.93(s, 3H), 2.81(s, 3H), 6.93–7.02(m, 2H), 7.15–7.63(m, 7H), 8.56(bra, 1H)

m/e: 288(M$^+$)

2) Preparation of 1-(2-methylphenyl)-4-chloro-6-methylpyrrolo[3,2-c]quinoline (X)

1-(2-methylphenyl)-4-oxo-6-methyl-4,5-dihydro pyrrolo [3,2-c]quinoline (1.16 g, 4.0 mmol) was dissolved in 10 ml of phosphoryl chloride (POCl$_3$) and heated for 2 hours. The reaction mixture was stirred at room temperature for 30 minutes after cooling and addition of ice water. The reaction mixture was extracted with methylene chloride (20 ml×3). After washing with water (15 ml×3), the organic layer was dried by anhydrous magnesium sulfate and filtered, and concentrated under reduced pressure. The residue was purified by silica gel chromatography to obtain 1.12 g of desired compound as an oil in 91% of yield.

mp: 139°–142° C.

¹H NMR(CDCl₃, 200 MHz): δ 1.92(s, 3H), 2.32(s, 3H), 6.91(d, J=3.1 Hz, 1H), 6.94(d, J=3.1 Hz, 1H), 7.07 (d, J=2.7 Hz, 1H), 7.14(d, J=3.0 Hz, 1H), 7.31–7.60(m, 5H)

m/e: 306(M⁺)

3) preparation of 1-(2-methylphenyl)-4-[(2-hydroxyethyl)amino]-6-methylpyrrolo[3,2-c]quinoline (III)

1-(2-methylphenyl)-4-chloro-6-methylpyrrolo [3,2-c] quinoline (306 mg, 1.0 mmol) was dissolved in 10 ml of ethanolamine in a pressure tube and heated at 150° C. for 3 hours. After removal of the reaction solvent under reduced pressure and diluted in 20 ml of methylene chloride, the residue was dried by anhydrous magnesium sulfate and filtered, and concentrated under reduced pressure. The residue was purified by silica gel chromatography to obtain 236 mg of desired compound as solid in 72% of yield.

mp: 187°–189° C.

¹H NMR(CDCl₃, 200 MHz): δ 1.93(s, 3H), 2.69(s, 3H), 3.91–3.99(m, 4H), 5.61(bra, 1H), 6.67–7.01(m, 5H), 7.25–7.52(m, 5H)

m/e: 331(M⁺)

EFFECT OF THE INVENTION

As apparent from the above examples, the process for preparing 1-aryl-4-oxopyrrolo[3,2-c]quinoline derivatives I according to the present invention adopts reagents of low cost under mild reaction conditions and the compound I may be prepared from the compound II in a single step. Especially, the preparation process according to the present invention can introduce various substituents such as R¹, R², R³ and R₄ which have not been introduced in the prior art. Therefore, according to the present process, the compound IV which is a reversible inhibitor of the gastric acid secretion and has various substituents may be prepared safely and economically in high yield from the 1-aryl-4-oxopyrrolo[3,2-c]quinoline derivatives.

What is claimed is:

1. A process for preparing a 1-aryl-4-oxopyrrolo [3,2-c] quinoline compound as represented by formula I, by direct reaction in a single step of 4-oxofuro[3,2-c]quinoline compound as represented by formula II with an aniline as represented by formula III:

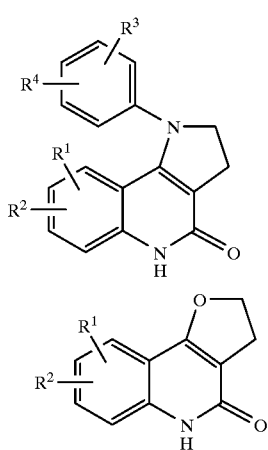

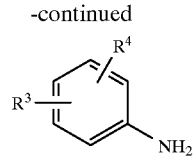

wherein, R¹ is same or different from R². R¹ and R² are respectively hydrogen, lower alkyl group of C₁–C₄, lower alkoxy group of C₁–C₄, lower alkylthio group of C₁–C₄, lower haloalkoxy group of C₁–C₄, trifluoromethyl group, hydroxyalkoxy group of C₁–C₄, halogen, or hydroxy group; and R³ is same or different from R⁴, R³ and R⁴ are respectively hydrogen, lower alkyl group of C₁–C₄, lower alkoxy group of C₁–C₄, lower alkylthio group of C₁–C₄ lower haloalkyl group of C₁–C₄, trifluoromethyl group, hydroxy group, amino group, or halogen.

2. The process as claimed in claim 1, wherein R¹, R², R³ and R⁴ are same or different from each other and are respectively hydrogen, methyl or methoxy.

3. The process as claimed in claim 1, wherein R¹, R², R³ and R⁴ are same or different from each other and are respectively methyl, hydroxy or fluoro.

4. The process as claimed in claim 1, wherein R¹, and R² are respectively hydrogen or hydroxyalkoxy group, and R³ and R⁴ are same or different from each other and are respectively hydrogen, methyl or methoxy.

5. The process as claimed in claim 1, wherein R¹, and R² are respectively hydrogen or hydroxyalkoxy group, and R³ and R⁴ are same or different from each other and are respectively methyl, hydroxy or fluoro.

6. The process as claimed in claim 1, wherein the reaction solvent is selected from dimethyl formamide, dimethylsulfoxide, diphenyl ether, xylene, butyl alcohol, phenol, ethylene glycol, diethylene glycol, triethylene glycol, polyetylene glycol, and ethylene glycol monomethyl ether.

7. The process as claimed in claim 1, wherein the reaction temperature is 70°–300° C.

8. The process as claimed in claim 1, wherein the amount of the aniline compounds used is 1–3 equivalents for the preparation of a 4-oxofuro[3,2-c]quinoline compound.

9. A process for preparing the compound as represented by formula IV

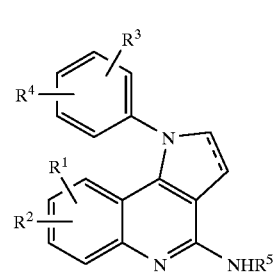

-continued

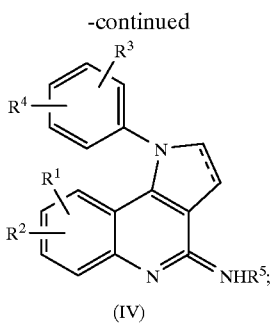

(IV)

by reacting a 4-oxofuro[3,2-c]quinoline compound as represented by formula II with an aniline compound as represented by formula III in a reaction solvent through a single step in accordance with claim 1 to obtain a compound as represented by formula I, adding $POCl_3$ to the compound I to obtain compound as represented by formula VIII,

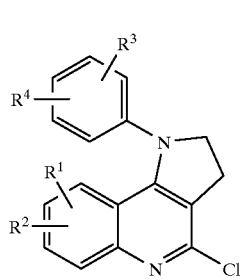

(VIII)

and adding alkylamine to the compound VIII.

10. The process as claimed in claim 1, wherein formula I is prepared in higher than 70% yield.

11. The process as claimed in claim 6, wherein the solvent is selected from alcoholic solvents having a boiling point of about 150°–280° C.

12. The process as claimed in claim 11, wherein the solvent is selected from phenol, ethylene glycol, diethylene glycol or polyethylene glycol.

13. The process as claimed in claim 1, wherein the reaction is performed under inert atmosphere.

14. The process as claimed in claim 13, wherein the reaction is performed under argon or nitrogen atmosphere.

15. The process as claimed in claim 1, comprising the additional step of using, as a reaction catalyst, p-toluenefulfonic acid or p-toluenesulfonic acid pyridine salt.

16. The process as claimed in claim 7, wherein the reaction temperature is 150°–280° C.

17. The process as claimed in claim 1, wherein reaction time is 7–20 hours.

18. The process as claimed in claim 16, wherein reaction time is 7–20 hours.

* * * * *